(12) United States Patent
Son et al.

(10) Patent No.: US 12,117,457 B2
(45) Date of Patent: Oct. 15, 2024

(54) METHOD FOR SIMULTANEOUS ANALYSIS OF NEUROTRANSMITTERS AND THEIR METABOLITES BASED ON DERIVATIZATION

(71) Applicant: KOREA INSTITUTE OF SCIENCE AND TECHNOLOGY, Seoul (KR)

(72) Inventors: Junghyun Son, Seoul (KR); Yoeseph Cho, Seoul (KR); Oh-Seung Kwon, Seoul (KR); Hana Park, Seoul (KR); Jin Woo Park, Seoul (KR); Yejin Lee, Seoul (KR); Seongeun Jeon, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 316 days.

(21) Appl. No.: 17/219,023

(22) Filed: Mar. 31, 2021

(65) Prior Publication Data

US 2021/0389336 A1    Dec. 16, 2021

(30) Foreign Application Priority Data

Jun. 4, 2020   (KR) .................. 10-2020-0067399

(51) Int. Cl.
*G01N 33/94*   (2006.01)

(52) U.S. Cl.
CPC ..... *G01N 33/9406* (2013.01); *G01N 33/9413* (2013.01); *G01N 33/942* (2013.01); *G01N 33/9426* (2013.01); *G01N 33/944* (2013.01)

(58) Field of Classification Search
CPC .......... G01N 33/9406; G01N 33/9413; G01N 33/942; G01N 33/9426; G01N 33/944;
(Continued)

(56) References Cited

FOREIGN PATENT DOCUMENTS

| CN | 105866303 A | * | 8/2016 | ............ G01N 30/06 |
| KR | 1020170134905 A | | 12/2017 | |
| KR | 101825035 B1 | | 2/2018 | |

OTHER PUBLICATIONS

Mishra, Arun, et al. "Simultaneous determination of epinephrine and norepinephrine by high performance liquid chromatography." Scientia Pharmaceutica 77.2 (2009): 367-374. (Year: 2009).*
(Continued)

*Primary Examiner* — Jill A Warden
(74) *Attorney, Agent, or Firm* — Rabin & Berdo, P.C.

(57) ABSTRACT

Disclosed is a method for simultaneous analysis of neurotransmitters and/or their metabolites. The method includes (a) separating analytes including a plurality of neurotransmitters and/or their metabolites from a sample selected from body tissues, body fluids, secretions, and excretions, (b) derivatizing the analytes with ethyl chloroformate to obtain derivatives of the plurality of neurotransmitters and/or their metabolites, (c) separating the derivatives of the plurality of neurotransmitters and/or their metabolites by liquid chromatography, and (d) subjecting the separated derivatives of the neurotransmitters or their metabolites to multiple reaction monitoring (MRM) using a mass spectrometer. According to the method, a plurality of neurotransmitters in a very small amount of sample can be simultaneously analyzed in an accurate and rapid manner based on derivatization to increase the stability and ionization efficiency of the substances.

15 Claims, 6 Drawing Sheets

(58) Field of Classification Search
CPC .............. G01N 2560/00; G01N 30/06; G01N 30/7233; G01N 2030/067; G01N 2030/8813

See application file for complete search history.

(56) References Cited

OTHER PUBLICATIONS

Krull, I. S., et al. Handbook of Methods and Instrumentation in Separation Science, vol. 1—Liquid Chromatography: Derivatization. (2000): 379-386. Retrieved from: <https://app.knovel.com/hotlink/pdf/id:kt00BYXWV1/handbook-methods-instrumentation/handbook-m-introduction-19>. (Year: 2000)*

Farmer et al. "15.5: Aromatic Heterocycles—Pyridine and Pyrrole." LibreTexts (2022). Retrieved from: <https://chem.libretexts.org/Bookshelves/Organic_Chemistry/Organic_Chemistry_(Morsch_et_al.)/15%3A_Benzene_and_Aromaticity/15.05%3A_Aromatic_Heterocycles-_Pyridine_and_Pyrrole>. (Year: 2022).*

Bartley et al. April 2016. NIOSH Manual of Analytical Methods (NMAM) (5th Edition)—3. Measurement Uncertainty and NIOSH Method Accuracy Range. U.S. Department of Health and Human Services, CDC/NIOSH Office of Mine Safety and Health Research. Retrieved from Knovel. (Year: 2016).*

Ju-Young Park et al., "Simultaneous Measurement of Serotonin, Dopamine and Their Metabolites in Mouse Brain Extracts by High-Performance Liquid Chromatography with Mass Spectrometry Following Derivatization with Ethyl Chloroformate", Biol. Pharm. Bull., Nov. 29, 2012, pp. 252-258, vol. 36, No. 2.

Arun Mishra et al., "Simultaneous Determination of Epinephrine and Norepinephrine by High Performance Liquid Chromatography", Scientia Pharmaceutica, Apr. 4, 2009, pp. 367-374, vol. 77.

* cited by examiner

METHOD FOR SIMULTANEOUS ANALYSIS OF NEUROTRANSMITTERS AND THEIR METABOLITES BASED ON DERIVATIZATION

CROSS-REFERENCE TO RELATED APPLICATIONS

This application claims priority under 35 U.S.C. § 119 to Korean Patent Application No. 10-2020-0067399 filed on Jun. 4, 2020 in the Korean Intellectual Property Office, the disclosure of which is incorporated herein by reference in its entirety.

BACKGROUND OF THE INVENTION

1. Field of the Invention

The present invention relates to a method for simultaneous analysis of neurotransmitters and their metabolites, and more specifically to a method for simultaneous analysis of neurotransmitters and their metabolites with improved analytical sensitivity based on derivatization.

2. Description of the Related Art

Neurotransmitters are molecules that act as mediators transmitting signals between neurons at chemical synapses. Neurotransmitters are synthesized in presynaptic neurons and released from the axon terminals. The released neurotransmitters bind to and activate their corresponding neurotransmitter receptors present in neurons, muscles, secretory cells, etc. to generate new signals.

A molecule as a neurotransmitter should meet the following requirements. First, the molecule should be synthesized and stored in presynaptic neurons. Second, the molecule should be secreted from the presynaptic axon terminals when stimulated. Third, when treated experimentally, the neurotransmitter secreted from presynaptic neurons should produce the same response that is induced in postsynaptic neurons. The neurotransmitter meeting these requirements exists in various forms such as amino acids, amines, and peptides.

After storage in synaptic vesicles in the axon terminals, neurotransmitters are released into the synaptic cleft by the activation of neurons, diffuse, and bind to neurotransmitter receptors present in postsynaptic cells. This process is called synaptic transmission.

Neurotransmitters synthesized at chemical synapses should be stored in a state ready for secretion. Neurotransmitters are synthesized in as many forms as their types. Glutamic acid and glycine are amino acids abundant in the body while other neurotransmitters are produced in and released from neurons, which require specific synthases. Enzymes necessary for the synthesis of γ-aminobutyric acid and amine neurotransmitters are produced in the cell body and transported to the axon terminals, where neurotransmitters are synthesized locally. The produced neurotransmitters are stored at high concentrations in synaptic vesicles. The storage of the neurotransmitters requires special transporter proteins present in the endoplasmic reticulum membrane. Peptide neurotransmitters are produced as precursors in the form of long peptides in the rough endoplasmic reticulum of the cell body and finely cleaved into smaller active neuropeptides in the Golgi apparatus. Secretory vesicles carrying the neuropeptides separated from the Golgi apparatus are transported to the axon terminals.

Neurotransmitters stored in synaptic vesicles or secretory granules undergo a series of release processes triggered by action potentials arriving at the axon terminals. When the axon terminal is depolarized by an action potential, voltage-dependent calcium channels are opened and calcium enters the cell. The increased calcium concentration induces exocytosis of synaptic vesicles and the neurotransmitters contained in the synaptic vesicles are released into the synaptic cleft. The membrane of the synaptic vesicles fused with the cell membrane of the synaptic terminal is recycled into vesicles through endocytosis. The recycled vesicles are reloaded with neurotransmitters. Secretory granules are also released by exocytosis but their release require a higher frequency of continuous action potentials than the release of synaptic vesicles.

Neurotransmitters released into the synaptic cleft need to be removed for next synaptic transmission. Neurotransmitters are passively removed by diffusion. However, neurotransmitters are often reabsorbed into the axon terminals by neurotransmitter transport proteins present in synaptic terminals or degraded by enzymes in the synaptic cleft in a more active manner.

Neurotransmitters play a physiologically important role in the body and can cause various diseases. Thus, it is essential to accurately measure neurotransmitters that can indicate the diagnosis and treatment stages of diseases. However, many neurotransmitters are difficult to accurately analyze due to their low stability and poor ionization efficiency.

PRIOR ART DOCUMENTS

Patent Documents

Korean Patent Publication No. 10-2017-0134905

SUMMARY OF THE INVENTION

The present invention has been made in an effort to solve the above-described problems and an object of the present invention is to provide a method for simultaneous analysis of a plurality of neurotransmitters and their metabolites in a very small amount of sample in a rapid and accurate manner based on derivatization to increase the stability and ionization efficiency of the substances.

According to an aspect of the present invention, there is provided a method for simultaneous analysis of neurotransmitters and/or their metabolites, including (a) separating analytes including a plurality of neurotransmitters and/or their metabolites from a sample selected from body tissues, body fluids, secretions, and excretions, (b) derivatizing the analytes with ethyl chloroformate to obtain derivatives of the plurality of neurotransmitters and/or their metabolites, (c) separating the derivatives of the plurality of neurotransmitters and/or their metabolites by liquid chromatography, and (d) subjecting the separated derivatives of the neurotransmitters or their metabolites to multiple reaction monitoring (MRM) using a mass spectrometer.

The neurotransmitters and/or their metabolites may be selected from tyrosine (Tyr), 3,4-dihydroxy-1-phenylalanine (L-DOPA), dopamine (DA), 3,4-dihydroxyphenylacetic acid (DOPAC), 3-methoxytyramine (3-MT), homovanillic acid (HVA), norepinephrine (NE), epinephrine (EP), normetanephrine (NMN), 3,4-dihydroxyphenyl glycol (DHPG), metanephrine (MN), 3-methoxy-4-hydroxyphenylglycol (MHPG), 3-methoxy-4-hydroxymandelic acid (VMA), tyramine (TA), octopamine (OA), kynurenine (Kyn), tryptophan (Trp), 5-hydroxytryptophan (5-HTP), serotonin (5-HT), 5-hydroxyindole-3-acetic acid (5-HIAA), glutamine (Gln), glutamate (Glu), γ-aminobutyric acid (GABA), and acetylcholine (ACh).

Step (a) may include (a-1) adding an aqueous solution of acetic acid and ammonium acetate to a sample selected from body tissues, body fluids, secretions, and excretions to extract the sample and (a-2) centrifuging the extract to separate the supernatant in which analytes including a plurality of neurotransmitters and/or their metabolites are present.

The sample may be a brain tissue or urine sample.

The aqueous solution of acetic acid and ammonium acetate may have a pH of 4 to 6.

In substep (a-1), the extraction may be performed by ultrasonic extraction.

Step (a) may further include diluting the separated analytes with an aqueous solution of acetic acid and ammonium acetate after substep (a-2).

During the derivatization in step (b), ethyl chloroformate may react with and replace hydroxyl and/or amine groups of the neurotransmitters and/or their metabolites to obtain derivatives of the neurotransmitters and/or their metabolites.

Step (b) may include (b-1) adding a mixed solution of ethanol and pyrimidine and ethyl chloroformate to the separated analytes to derivatize the analytes and (b-2) adding an organic solvent to the derivatized analytes, extracting the derivatives of the neurotransmitters and/or their metabolites by liquid-liquid extraction, and concentrating the derivatives.

In substep (b-1), the ethanol and the pyrimidine may be present in a weight ratio of 90:10 to 70:30 in their mixed solution.

In substep (b-1), the ethanol-pyrimidine mixed solution and the ethyl chloroformate may be added in a weight ratio of 100:5 to 100:20.

In substep (b-1), the derivatization may be performed for 3 to 10 minutes.

In substep (b-1), the derivatization may be performed at room temperature.

In substep (b-2), the organic solvent may be selected from diethyl ether, methyl tert-butyl ether, ethyl acetate, hexane, chloroform, dichloromethane, and toluene.

In step (c), the liquid chromatography may use a mobile phase selected from an aqueous solution of formic acid, an aqueous solution of acetic acid, and a mixed aqueous solution of acetic acid and ammonium acetate.

In step (c), the liquid chromatography may use a C18 column as a stationary phase.

In step (c), the liquid chromatography may be performed for 3 to 10 minutes.

In step (d), the multiple reaction monitoring (MRM) may be performed to simultaneously analyze two or more neurotransmitters and/or their metabolites selected from tyrosine (Tyr), 3,4-dihydroxy-1-phenylalanine (L-DOPA), dopamine (DA), 3,4-dihydroxyphenylacetic acid (DOPAC), 3-methoxytyramine (3-MT), homovanillic acid (HVA), norepinephrine (NE), epinephrine (EP), normetanephrine (NMN), 3,4-dihydroxyphenyl glycol (DHPG), metanephrine (MN), 3-methoxy-4-hydroxyphenylglycol (MHPG), 3-methoxy-4-hydroxymandelic acid (VMA), tyramine (TA), octopamine (OA), kynurenine (Kyn), tryptophan (Trp), 5-hydroxytryptophan (5-HTP), serotonin (5-HT), 5-hydroxyindole-3-acetic acid (5-HIAA), glutamine (Gln), glutamate (Glu), γ-aminobutyric acid (GABA), and acetylcholine (ACh).

The multiple reaction monitoring (MRM) may be performed by detecting hydrogen ions ($H^+$) or ammonium ions ($NH_4^+$) of the neurotransmitters and/or their metabolites.

The method of the present invention uses ethyl chloroformate suitable for and rapidly reactive with analytes to extract the analytes by liquid-liquid extraction and analyzes the extract by liquid chromatography-mass spectrometry using a C18 column, with the result that neurotransmitters and their metabolites can be detected with greatly increased sensitivity based on derivatization. Therefore, the method of the present invention has a very low limit of detection compared to conventional analytical methods and enables the detection of analytes in a very small amount of sample. According to the method of the present invention, the polarities of neurotransmitters and their metabolites can be reduced by derivatization and the selectivities to and separation efficiencies of neurotransmitters and their metabolites in a C18 column can be increased by the use of an improved analytical solvent, etc., eventually enabling simultaneous detection of 24 types of analytes in a significantly reduced analysis time (5 minutes). Therefore, the method of the present invention can be used in various applications, including clinical applications.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Several aspects and various embodiments of the present invention will now be described in more detail.

Embodiments of the present invention will be described in detail with reference to the accompanying drawings such that those skilled in the art can readily practice the invention.

However, the following description is not intended to limit the present invention to specific embodiments. In the description of the present invention, certain detailed explanations of related art are omitted when it is deemed that they may unnecessarily obscure the essence of the invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises", "comprising", "includes", "including", "has" or "having" as used herein specify the presence of stated features, numbers, steps, operations, components or combinations thereof and do not preclude the possibility that one or more other features, numbers, steps, operations, components or combinations thereof may exist or may be added.

Figure 1:
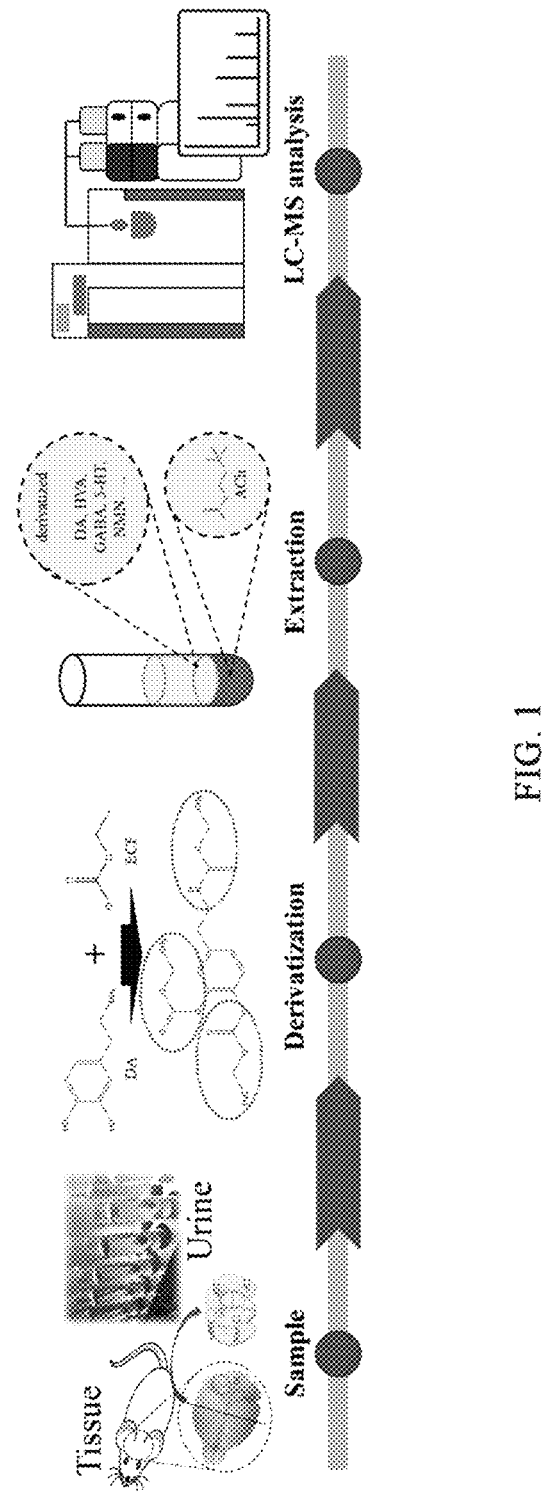
FIG. 1 is a diagram sequentially showing an embodiment of a method for simultaneous analysis of neurotransmitters and/or their metabolites according to the present invention.
Figure 2:
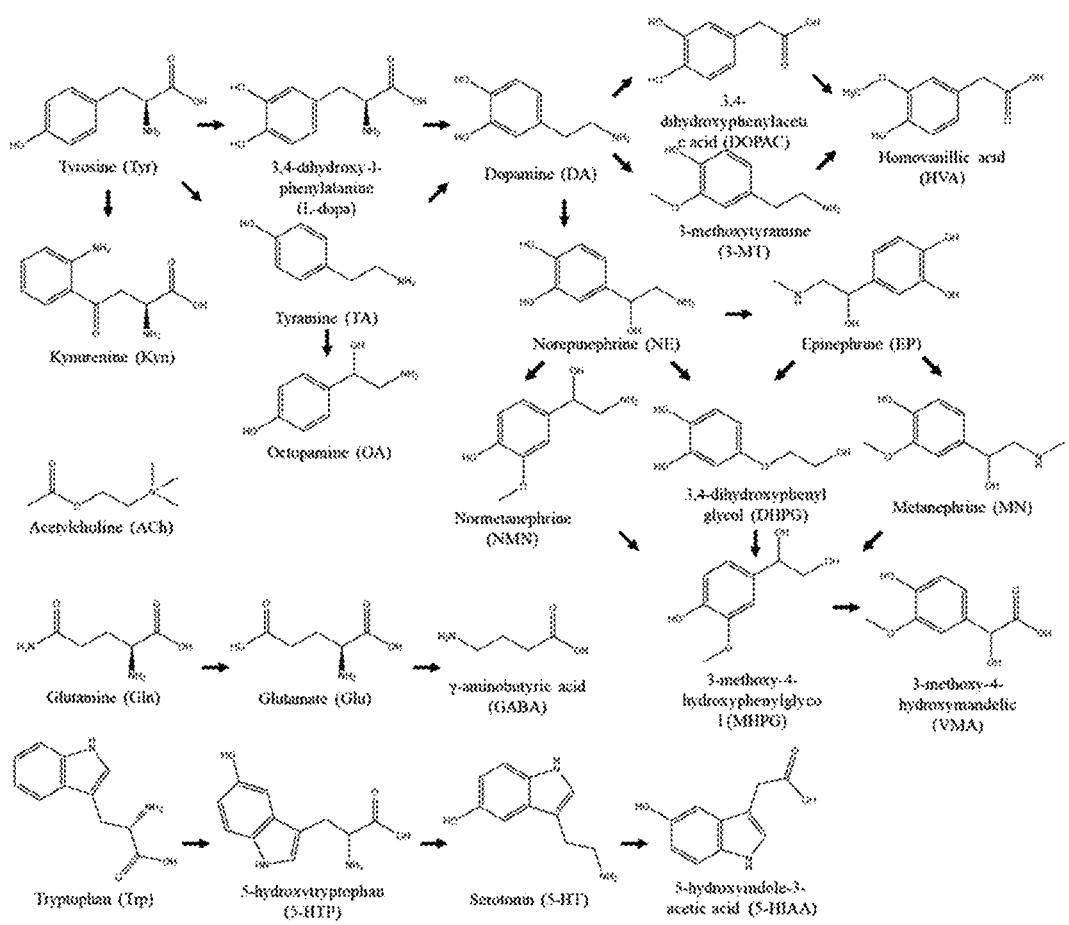
FIG. 2 shows 24 types of neurotransmitters and their metabolites applied to the present invention and their metabolic processes.
Figure 3:
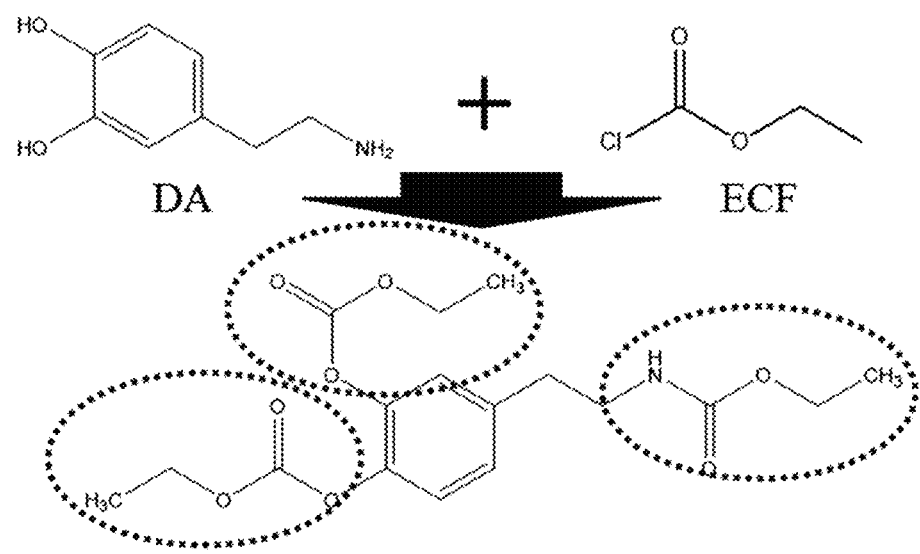
FIG. 3 shows an exemplary derivatization reaction of dopamine as a neurotransmitter.

FIG. 1 is a diagram sequentially showing an embodiment of a method for simultaneous analysis of neurotransmitters and/or their metabolites according to the present invention, FIG. 2 shows 24 types of neurotransmitters and their metabolites applied to the present invention and their metabolic processes, and FIG. 3 shows an exemplary derivatization reaction of dopamine as a neurotransmitter.

A method for simultaneous analysis of neurotransmitters and/or their metabolites according to the present invention will be described with reference to FIG. 1.

First, analytes including a plurality of neurotransmitters and/or their metabolites are separated from a sample selected from body tissues, body fluids, secretions, and excretions (step a).

As shown in FIG. 2, the neurotransmitters and/or their metabolites may be selected from tyrosine (Tyr), 3,4-dihydroxy-1-phenylalanine (L-DOPA), dopamine (DA), 3,4-dihydroxyphenylacetic acid (DOPAC), 3-methoxytyramine (3-MT), homovanillic acid (HVA), norepinephrine (NE), epinephrine (EP), normetanephrine (NMN), 3,4-dihydroxyphenyl glycol (DHPG), metanephrine (MN), 3-methoxy-4-hydroxyphenylglycol (MHPG), 3-methoxy-4-hydroxymandelic acid (VMA), tyramine (TA), octopamine (OA), kynurenine (Kyn), tryptophan (Trp), 5-hydroxytryptophan (5-HTP), serotonin (5-HT), 5-hydroxyindole-3-acetic acid (5-HIAA), glutamine (Gln), glutamate (Glu), γ-aminobutyric acid (GABA), and acetylcholine (ACh).

Step a is preferably carried out in the following order.

First, an aqueous solution of acetic acid and ammonium acetate is added to a sample selected from body tissues, body fluids, secretions, and excretions to extract the sample (a-1).

The sample is preferably a brain tissue or urine sample, but the scope of the present invention is not limited thereto. For example, the sample may be collected from any tissue containing neurotransmitters and/or their metabolites that need to be analyzed.

The aqueous solution of acetic acid and ammonium acetate preferably has a pH in the range of 4 to 6, more preferably 4 to 5. Outside this pH range, the ability to detect analytes may deteriorate.

The extraction may be performed by ultrasonic extraction, but the scope of the present invention is not limited thereto. For example, any method that can be used to extract neurotransmitters and/or their metabolites with high efficiency is applicable.

Thereafter, the extract is centrifuged to separate the supernatant in which analytes including a plurality of neurotransmitters and/or their metabolites are present (a-2).

The separation of the supernatant enables the removal of substances interfering with analysis as well as the separation of analytes.

Step a may further include diluting the separated analytes with an aqueous solution of acetic acid and ammonium acetate.

Next, the analytes are derivatized with ethyl chloroformate to obtain derivatives of the plurality of neurotransmitters and/or their metabolites (step b).

During the derivatization reaction, the ethyl chloroformate reacts with and replace hydroxyl (—OH) and/or amine groups (—NH$_2$) of the neurotransmitters and/or their metabolites to form derivatives of the neurotransmitters and/or their metabolites.

This step is preferably carried out in the following way.

First, a mixed solution of ethanol and pyrimidine and ethyl chloroformate are added to the separated analytes to derivatize the analytes (b-1).

The ethanol and the pyrimidine are preferably present in a weight ratio of 90:10 to 70:30 in their mixed solution.

The ethanol-pyrimidine mixed solution and the ethyl chloroformate are preferably added in a weight ratio ranging from 100:5 to 100:20. The use of the ethanol, the pyrimidine, and the ethyl chloroformate within the range defined above allows the subsequent derivatization to proceed smoothly and quickly.

The derivatization may be performed for 3 to 10 minutes. The derivatization is preferably completed within 5 minutes.

The derivatization may be performed at room temperature.

Thereafter, an organic solvent is added to the derivatized analytes, the derivatives of the neurotransmitters and/or their metabolites are extracted by liquid-liquid extraction, and the derivatives are concentrated (b-2).

The organic solvent may be selected from diethyl ether, methyl tert-butyl ether, ethyl acetate, hexane, chloroform, dichloromethane, and toluene. The organic solvent is more preferably selected from diethyl ether and methyl tert-butyl ether. Methyl tert-butyl ether is even more preferable in terms of extraction efficiency.

Next, the derivatives of the plurality of neurotransmitters and/or their metabolites are separated by liquid chromatography (step c).

Preferably, the liquid chromatography uses a mobile phase selected from an aqueous solution of formic acid, an aqueous solution of acetic acid, and a mixed aqueous solution of acetic acid and ammonium acetate. More preferably, the liquid chromatography uses a mixed aqueous solution of acetic acid and ammonium acetate as a mobile phase.

Preferably, the liquid chromatography uses a C18 column as a stationary phase.

The liquid chromatography may be performed for 3 to 10 minutes. Preferably, the liquid chromatography takes 5 minutes for complete separation.

Finally, the separated derivatives of the neurotransmitters or their metabolites are subjected to multiple reaction monitoring (MRM) using a mass spectrometer (step d).

The multiple reaction monitoring (MRM) enables simultaneous analysis of two or more analytes selected from tyrosine (Tyr), 3,4-dihydroxy-1-phenylalanine (L-DOPA), dopamine (DA), 3,4-dihydroxyphenylacetic acid (DOPAC), 3-methoxytyramine (3-MT), homovanillic acid (HVA), norepinephrine (NE), epinephrine (EP), normetanephrine (NMN), 3,4-dihydroxyphenyl glycol (DHPG), metanephrine (MN), 3-methoxy-4-hydroxyphenylglycol (MHPG), 3-methoxy-4-hydroxymandelic acid (VMA), tyramine (TA), octopamine (OA), kynurenine (Kyn), tryptophan (Trp), 5-hydroxytryptophan (5-HTP), serotonin (5-HT), 5-hydroxyindole-3-acetic acid (5-HIAA), glutamine (Gln), glutamate (Glu), γ-aminobutyric acid (GABA), and acetylcholine (ACh).

Multiple reaction monitoring (MRM) is a technique for detecting a specific analyte based on the characteristics of product ions obtained as a result of cleavage of a precursor ion by collision energy.

Specifically, the multiple reaction monitoring (MRM) employed in the method of the present invention is performed to detect ions bonded with hydrogen ions (H$^+$) or ammonium ions (NH$_4^+$) of the neurotransmitters and/or their metabolites.

[Experimental Section]

Analytical Method (1) Selection of Analytes and Extraction of Samples

All 24 standards shown in FIG. 2 were purchased. Six of these standards were selected as internal standards based on their metabolic processes. The selected standards were DA, Glu, GABA, Ach, 5-HTP, and NE and their deuterated products were purchased.

Two brain tissue and urine samples were used.

Samples (each 2-100 mg) collected from different areas of brain tissue were placed in 1.5 ml analytical tubes. Analytes were extracted with 500 μl of a mixture of acetic acid and ammonium acetate from the tissue in an ultrasonic extractor for 20 sec. Ice was added to prevent a rise in temperature during extraction. Thereafter, the extract was centrifuged at 13000 rpm for 5 min to precipitate large molecules. The supernatant containing analytes was separated. The extracted tissue sample was appropriately diluted with 500 μl of a mixture of acetic acid and ammonium acetate, followed by pretreatment. The volume of the mixture of acetic acid and ammonium acetate varied depending on the weight of the sample.

The same matrix used in the tissue sample was applied to the urine sample. The urine sample was diluted 10- or 100-fold with 500 μl of a mixture of acetic acid and ammonium acetate to a concentration suitable for detection with an instrument before use.

(2) Pretreatment by Derivatization

The pretreatment is largely divided into two processes. The first process is to modify the structures of the substances based on derivatization. The second process is to extract and concentrate the modified substances for injection into an instrument. First, the internal standards were mixed with each sample to compensate for possible errors during pretreatment such that their concentration was 500 ng/ml, and 10 μl of the internal standards were added to the mixture.

200 μl of a mixture of ethanol and pyrimidine (4:1) and 20 μl of ethyl chloroformate (ECF) were added to the sample in the form of an aqueous solution containing the analytes to derivatize the analytes. Derivatization of the analytes was completed very quickly 5 min) at room temperature.

After derivatization, 2 ml of methyl tert-butyl ether (MTBE) as an extraction solvent was added to the sample, followed by vortex mixing for 1 min. At this time, the derivatized substances moved from the aqueous layer to the MTBE layer. Thereafter, centrifugation was performed at 2500 rpm for 5 min to primarily separate the organic layer. After cooling to −35° C., the aqueous layer and the organic layer were separated. The organic layer was evaporated using a nitrogen evaporator to remove the organic solvent, redissolved in a mixture of 0.01% acetic acid & 1 mM ammonium acetate in D.W and acetonitrile (ACN) (1:1), and transferred to an analytical vial. The underivatized analytes such as Ach were contained in the aqueous layer. 200 μl of the aqueous layer was transferred to an analytical vial without purification.

(3) LC-MS Analysis

The pretreated sample was analyzed by LC-MS. Vanquish and Altis available from Thermo were used for LC and MS, respectively. The analysis time per sample was set to 5 min, and the LC and MS conditions were set based on the analysis time. A mixture of A) 0.01% acetic acid & 1 mM ammonium acetate in DW and B) ACN was used as a mobile phase for LC. A solvent gradient was formed by changing the proportion of B) ACN as follows. The proportion of B) CAN was initially set to 5%, maintained at 5% until 0.5 min, raised to 50% from 0.5 min until 1 min, maintained at 50% until 3 min, raised to 95% from 3 min until 3.5 min, maintained at 95% until 4 min, and decreased to 5% at 4 min, and maintained at 5% until 5 min. A Kinetex C18 column available from Phenomenex was used as a stationary phase and the temperature was set to 35° C. The mobile phase was allowed to flow at a rate of 0.5 ml/min and 10 μl of the sample was injected for separation of the substances. The MS was operated in the ESI positive mode to analyze all derivatized substances. The source conditions were as follows: Spray voltage=4.5 kV; sheath gas=60, aux gas=15, sweep gas=2 arbitrary units; ion transfer tube temperature=300, vaporizer temperature=300° C. The MS was operated in the selected reaction monitoring (SRM) mode to detect [M+H]$^+$ and [M+NH$_4$]$^+$ for all 24 analytes. The cycle time was set to 0.5 sec so as to ensure a sufficient dwell time. The substances were detected in the multiple reaction monitoring (MRM) mode based on the masses of precursor and product ions. The mass of the product ions of each substance and the optimal collision energy were determined based on a search for standards.

(4) Quantitative Evaluation

The inventive method was applied to actual samples to quantitatively evaluate neurotransmitters in vivo and compare and analyze the concentrations of neurotransmitters in different areas of the samples. Neurotransmitters and their metabolites in different areas of a mouse brain tissue were quantitatively evaluated. Neurotransmitters and their metabolites in a urine sample were quantitatively evaluated. Calibration curves for each sample were drawn using standards at at least five concentrations, including detection concentrations. The actual amounts detected in the sample were calibrated to internal standards and back-substituted into the calibration curves to estimate the concentrations.

Analytical Results (1) Conditions and Chromatograms of Analytes

A standard for each substance was derivatized and directly injected into a mass spectrometer. The mass of the precursor ions for the substituted structures and the mass of the product ions generated by the application of optimal energy (collision energy, CE) were measured. The conditions of the analytes are shown in Table 1.

TABLE 1

| Compound | Precursor (m/z) | Product (m/z) | CE (V) |
|---|---|---|---|
| Ach | 146.1 | 87 | 15 |
| d4-ACh | 150.1 | 91 | 15 |
| GABA . . . [M + H] | 204.1 | 158 | 10 |
| GABA . . . [M + NH4] | 221.1 | 158 | 10 |
| Gln . . . [M + H] | 276.1 | 230 | 10 |
| TA . . . [M + H] | 282.1 | 236 | 10 |
| HVA . . . [M + H] | 283.1 | 137 | 14 |
| 5HIAA . . . [M + H] | 292.1 | 218 | 14 |
| Gln . . . [M + NH4] | 293.1 | 276 | 8 |
| TA . . . [+ NH4] | 299.1 | 286 | 13 |
| HVA . . . [M + NH4] | 300.1 | 187 | 20 |
| Trp . . . [M + H] | 305.1 | 231 | 15 |
| 5HIAA . . . [M + NH4] | 309.1 | 218 | 17 |
| 3MT . . . [M + H] | 312.1 | 266 | 10 |
| 5HT . . . [M + H] | 321.1 | 203 | 17 |
| Trp . . . [M + NH4] | 322.1 | 305 | 9 |
| 3MT . . . [M + NH4] | 329.1 | 266 | 14 |
| 5HT . . .[M + NH4] | 338.1 | 321 | 8 |
| DOPAC . . .[M + H] | 341.1 | 123 | 24 |
| MN . . . [M + H] | 342.1 | 324 | 10 |
| Tyr . . . [M + H] | 354.1 | 248 | 17 |

TABLE 1-continued

| Compound | | Precursor (m/z) | Product (m/z) | CE (V) |
|---|---|---|---|---|
| DHBA | [M + H] | 356.1 | 123 | 24 |
| DOPAC | [M + NH4] | 358.1 | 123 | 28 |
| MN | [M + NH4] | 359.1 | 324 | 10 |
| DA | [M + H] | 370.1 | 180 | 18 |
| Tyr | [M + NH4] | 371.1 | 248 | 21 |
| DHBA | [M + NH4] | 373.1 | 356 | 10 |
| d4-DA | [M + H] | 374.1 | 184 | 20 |
| Kyn | [M + H] | 381.2 | 248 | 14 |
| OA | [M + NH4] | 387.1 | 280 | 10 |
| DA | [M + NH4] | 387.1 | 370 | 10 |
| VMA | [M + NH4] | 388.1 | 209 | 16 |
| d4-DA | [M + NH4] | 391.1 | 374 | 9 |
| 5HTP | [M + H] | 393.2 | 347 | 12 |
| Kyn | [M + NH4] | 398.2 | 381 | 8 |
| EP | [M + H] | 400.2 | 382 | 10 |
| MHPG | [M + H] | 401.1 | 383 | 8 |
| 5HTP | [M + NH4] | 140.2 | 347 | 16 |
| NMN | [M + NH4] | 417.2 | 310 | 10 |
| EP | [M + NH4] | 417.2 | 382 | 13 |
| MHPG | [M + NH4] | 418.1 | 383 | 13 |
| L-DOPA | [M + H] | 442.2 | 324 | 14 |
| NE | [M + H] | 458.2 | 368 | 10 |
| L-DOPA | [M + NH4] | 459.2 | 442 | 10 |
| NE | [M + NH4] | 475.2 | 368 | 10 |

Figure 4:
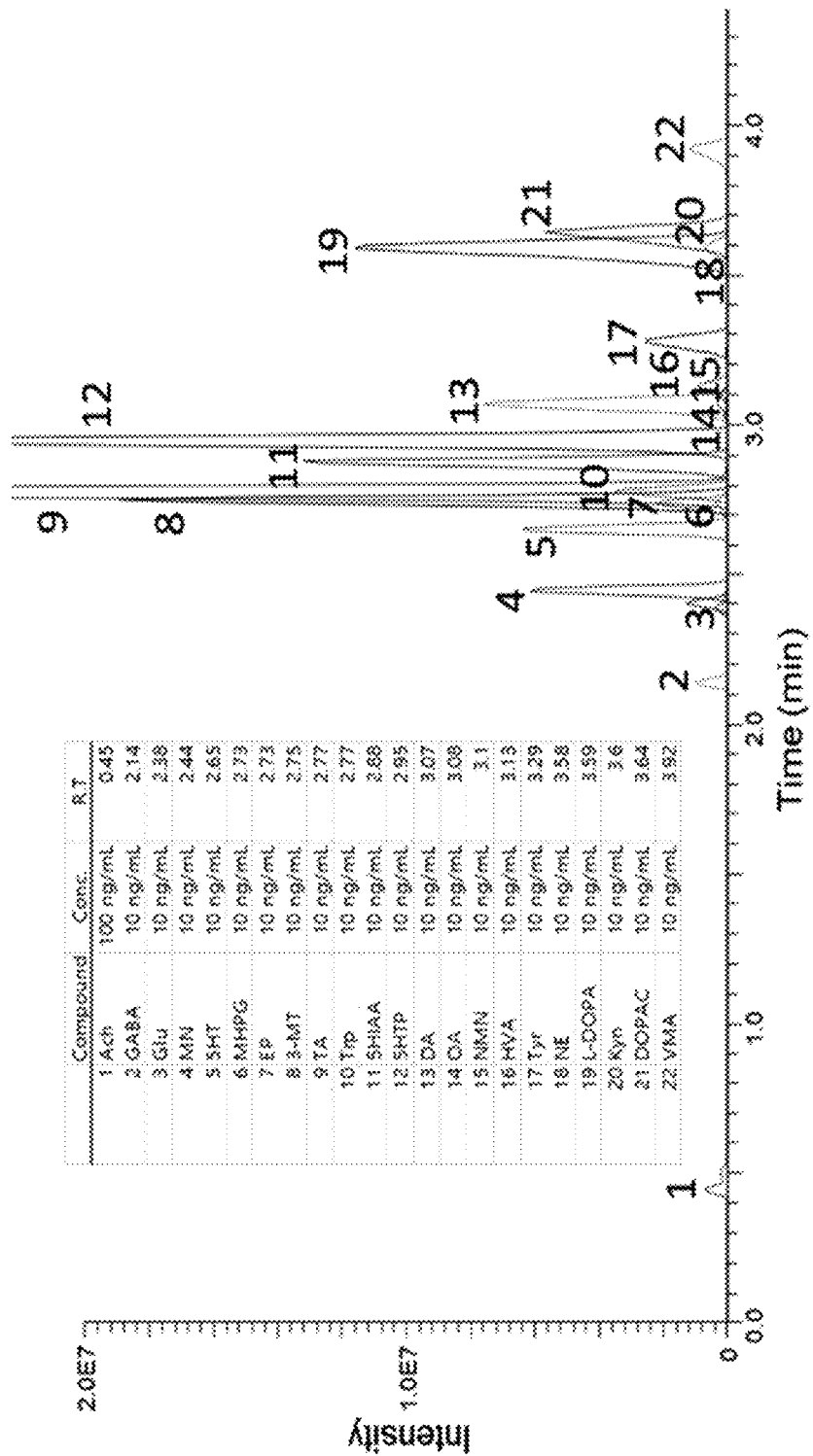
FIG. 4 shows retention times and chromatogram data of analytes, which were measured in the experimental section.

After the data of Table 1 were added to the multiple reaction monitoring (MRM) mode, LC-MS/MS analysis was performed. The retention times and chromatogram data of the analytes are shown in FIG. 4. All analytes were eluted between 2 and 4 min and were detected independently without interfering with other substances.

Figure 5:
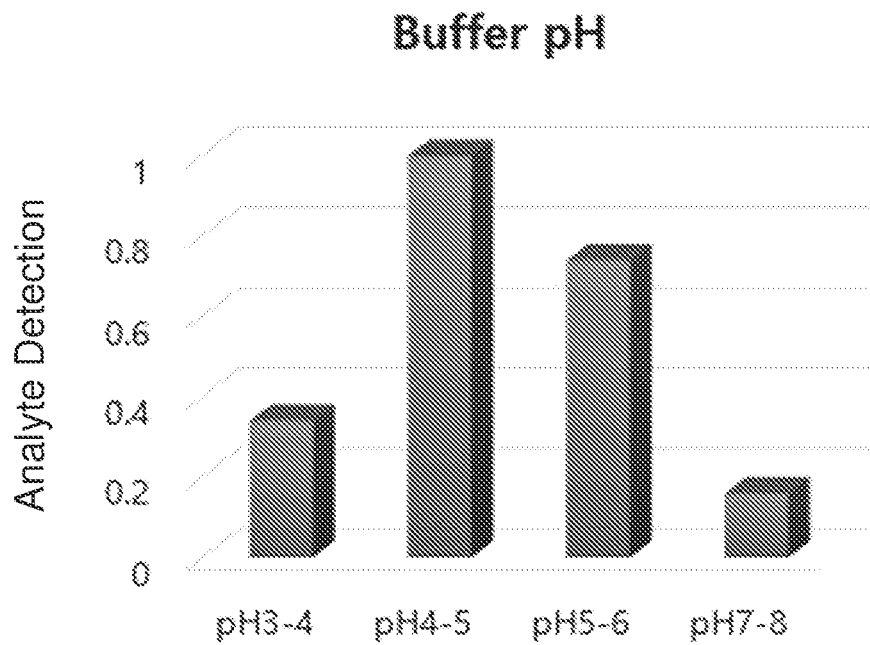
FIG. 5 shows the abilities to detect analytes depending on the pH of a solvent used to extract the analytes, which were measured in the experimental section.

(2) Selection of Buffer, Derivatization Time and Extraction Solvent of the Derivatized Analytes In most previous studies, a mixed solvent of organic solvents such as formic acid and acetonitrile (ACN) was added to a sample to extract and purify analytes. In order to find a buffer that is more effective than those used in previous studies, an experiment was conducted using different pH conditions and compositions. Considering that the analytes should be analyzed simultaneously rather than separately, the experiment focused on finding solvents that could lead to optimal detection of the analytes at their concentrations while enabling universal and appropriate extraction of all analytes. Mixing with an organic solvent causes low derivatization efficiency and makes it difficult for layer separation to occur when an extraction solvent is added after derivatization. Thus, organic solvents were excluded from this experiment and a search was conducted for DW-based buffers. As a result of the search, a mixed solvent of 0.01% acetic acid and 1 mM ammonium acetate showed the most optimal results in the concentration ranges of the analytes. The abilities to detect the analytes depending on the pH of the buffer were analyzed and are shown in FIG. 5. The pH of the buffer was adjusted with formic acid, acetic acid, and ammonium acetate in consideration of the pH range of the analytical column.

The derivatization rates of the analytes with the derivatization reagent after different reaction times (5 min, 10 min, 30 min) were measured. As a result, no significant differences were observed in the amounts of the analytes detected. Thus, the derivatization time was set to 5 min in the inventive method.

Figure 6:
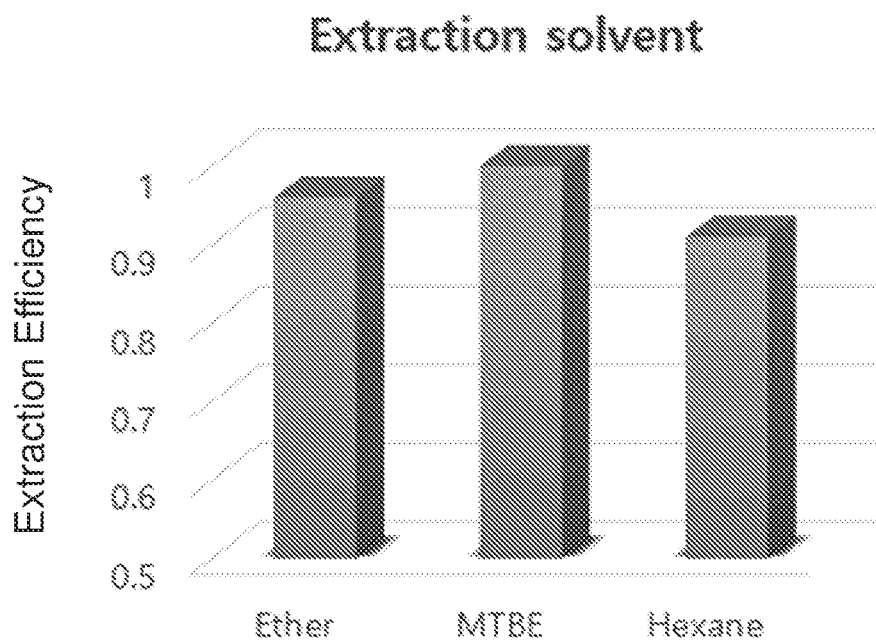
FIG. 6 compares the extraction efficiencies of different extraction solvents for derivatized analytes, which were measured in the experimental section.

The derivatized analytes were extracted with different solvents, including diethyl ether, hexane, and methyl tert-butyl ether (MTBE). FIG. 6 compares the extraction efficiencies of the extraction solvents. MTBE was found to be optimal for extracting the derivatized analytes. When the efficiency of MTBE was defined as 100%, the efficiencies of ether and hexane were ~96% and ~91%, respectively.

Figure 7:
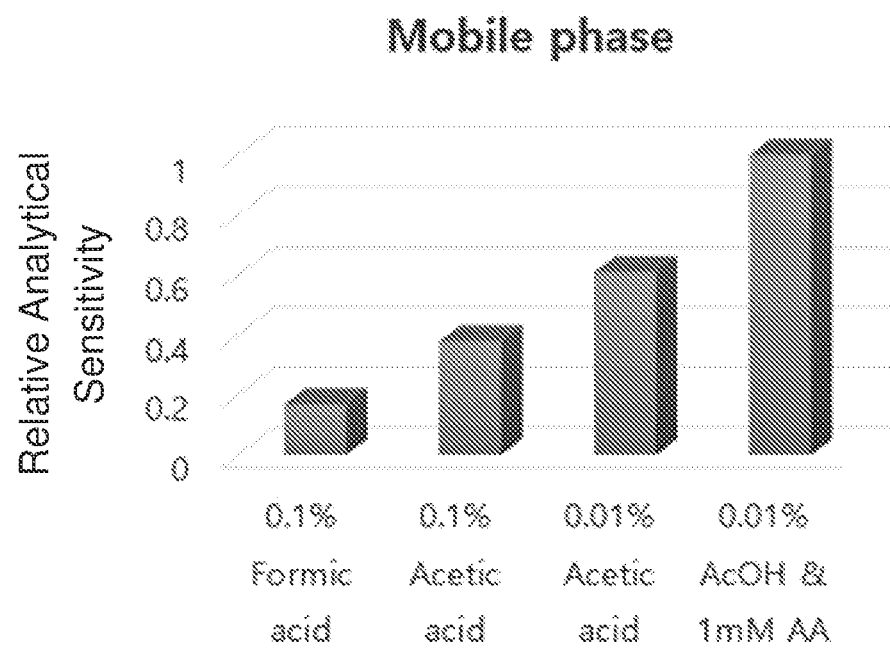
FIG. 7 shows the relative analytical sensitivities of liquid chromatography using different mobile phases according to the experimental section.

An experiment was conducted to determine an optimal resolution and an optimal analytical sensitivity on the instrument using different mobile phases: [1] 0.1% formic acid in DW, [2] 0.1% acetic acid in DW, [3] 0.01% acetic acid in DW, and [4] 0.01% acetic acid & 1 mM ammonium acetate. The same sample was analyzed using the instrument. The relative analytical sensitivities are shown in FIG. 7. Referring to FIG. 7, the highest sensitivity was obtained in the mobile phase [4] and no significant differences in resolution were found in the mobile phases [1]-[4].

(3) Evaluation of limits of detection

The linearity and limit of detection of the inventive method for each analyte were measured. The results are summarized in Table 2. Referring to Table 2, the linearities of the calibration curves for all analytes were ≥0.99.

TABLE 2

| Compounds | Range (ng/ml) | Linearity ($R^2$) | LOD (ng/ml) |
|---|---|---|---|
| 3MT | 0.005-0.500 | 0.9968 | <0.005 |
| 5HIAA | 0.010-1.000 | 0.9974 | <0.010 |
| 5HT | 0.020-2.000 | 0.9972 | <0.020 |
| 5HTP | 0.005-0.500 | 0.9977 | <0.005 |
| DA | 0.010-1.000 | 0.9992 | <0.010 |
| DOPAC | 0.020-2.000 | 0.9968 | <0.020 |
| EP | 0.020-2.000 | 0.9964 | <0.020 |
| HVA | 0.020-2.000 | 0.9966 | <0.020 |
| Kyn | 0.020-2.000 | 0.9977 | <0.020 |
| L-DOPA | 0.005-0.500 | 0.9979 | <0.005 |
| MHPG | 0.500-50.00 | 0.9931 | <0.500 |
| MN | 0.020-2.000 | 0.9941 | <0.020 |
| NE | 1.000-100.0 | 0.9943 | <1.000 |
| NMN | 0.200-20.00 | 0.9958 | <0.200 |
| OA | 0.100-10.00 | 0.9955 | <0.100 |
| TA | 0.002-0.200 | 0.9969 | <0.002 |
| Trp | 0.200-20.00 | 0.9939 | <0.200 |
| Tyr | 0.050-5.000 | 0.9995 | <0.050 |
| VMA | 0.020-2.000 | 0.997 | <0.020 |
| ACh | 1.000-100.0 | 0.9996 | <1.000 |

(4) Quantitative Evaluation Results

Different areas mPFC, dST, vST, CBL, and NAc of a mouse brain tissue were obtained for quantitative evaluation. The concentrations of neurotransmitters (ng/mg) in the areas are summarized in Table 3.

TABLE 3

| Compound | mPFC | dST | vST | CBL | NAc |
|---|---|---|---|---|---|
| DA | 0.07 | 32.4 | 18.7 | 0.01 | 9.96 |
| DOPAC | 0.05 | 11.9 | 6.99 | 0.13 | 6.9 |
| 3MT | — | 1.24 | — | — | 0.5 |
| HVA | 0.4 | 38.2 | 27 | 0.67 | 15.82 |
| 5HT | 0.4 | 1.16 | 2.08 | 0.03 | — |
| ACh | 1.17 | 2.97 | 2.33 | — | 1.3 |

The concentrations of neurotransmitters in urine are summarized in Table 5.

TABLE 4

| Compound | Conc. (ng/mL) | Compound | Conc. (ng/mL) |
|---|---|---|---|
| 3-MT | 0.016 | L-DOPA | 0.032 |
| 5HIAA | 1.616 | MHPG | 0.014 |
| 5HT | 0.097 | MN | 0.006 |

TABLE 4-continued

| Compound | Conc. (ng/mL) | Compound | Conc. (ng/mL) |
| --- | --- | --- | --- |
| 5HTP | 0.008 | NE | 0.135 |
| DA | 0.359 | NMN | 0.012 |
| DOPAC | 1.847 | OA | 0.244 |
| EP | 0.015 | TA | 0.064 |
| GABA | 24.738 | Trp | 31.399 |
| Glu | 2.534 | Tyr | N/F |
| HVA | 58.064 | VMA | 2.919 |
| Kyn | 0.760 | Ach | N/A |

Although the present invention has been described herein with reference to the foregoing embodiments, those skilled in the art will appreciate that various changes and modifications are possible by addition, modification, deletion or insertion of the elements without departing from the spirit of the present invention as disclosed in the accompanying claims. It is to be understood that such changes and modifications are within the scope of the present invention.

What is claimed is:

1. A method for simultaneous analysis of neurotransmitters and/or their metabolites, comprising (a) separating analytes comprising a plurality of neurotransmitters and/or their metabolites from a sample selected from body tissues, body fluids, secretions, and excretions, (b) derivatizing the analytes with ethyl chloroformate to obtain derivatives of the plurality of neurotransmitters and/or their metabolites, (c) separating the derivatives of the plurality of neurotransmitters and/or their metabolites by liquid chromatography, and (d) subjecting the separated derivatives of the neurotransmitters or their metabolites to multiple reaction monitoring (MRM) using a mass spectrometer, wherein the neurotransmitters and/or their metabolites have a limit of detection (LOD) of <0.1 ng/ml; and
   wherein step (b) comprises (b-1) adding a mixed solution of ethanol and pyrimidine and ethyl chloroformate to the separated analytes to derivatize the analytes and (b-2) adding an organic solvent to the derivatized analytes, extracting the derivatives of the neurotransmitters and/or their metabolites by liquid-liquid extraction, and concentrating the derivatives.

2. The method according to claim 1, wherein the neurotransmitters and/or their metabolites are selected from tyrosine (Tyr), 3,4-dihydroxy-I-phenylalanine (L-DOPA), dopamine (DA), 3,4-dihydroxyphenylacetic acid (DOPAC), 3-methoxytyramine (3-MT), homovanillic acid (HVA), epinephrine (EP), 3,4-dihydroxyphenyl glycol (DHPG), metanephrine (MN), 3-methoxy-4-hydroxymandelic acid (VMA), tyramine (TA), octopamine (OA), kynurenine (Kyn), 5-hydroxytryptophan (5-HTP), serotonin (5-HT), 5-hydroxyindole-3-acetic acid (5-HIAA), glutamine (Gln), glutamate (Glu), and γ-aminobutyric acid (GABA).

3. The method according to claim 1, wherein step (a) comprises (a-1) adding an aqueous solution of acetic acid and ammonium acetate to the sample selected from body tissues, body fluids, secretions, and excretions to extract the sample and (a-2) centrifuging the extract to separate the supernatant in which the analytes comprising a plurality of neurotransmitters and/or their metabolites are present.

4. The method according to claim 3, wherein the sample is a brain tissue or urine sample.

5. The method according to claim 3, wherein the aqueous solution of acetic acid and ammonium acetate has a pH of 4 to 6.

6. The method according to claim 1, wherein during the derivatization in step (b), ethyl chloroformate reacts with and replaces hydroxyl and/or amine groups of the neurotransmitters and/or their metabolites to obtain derivatives of the neurotransmitters and/or their metabolites.

7. The method according to claim 1, wherein in substep (b-1), the ethanol and the pyrimidine are present in a weight ratio of 90:10 to 70:30 in their mixed solution.

8. The method according to claim 1, wherein in substep (b-1), the ethanol-pyrimidine mixed solution and the ethyl chloroformate are added in a weight ratio of 100:5 to 100:20.

9. The method according to claim 1, wherein in substep (b-1), the derivatization is performed for 3 to 10 minutes.

10. The method according to claim 1, wherein in substep (b-2), the organic solvent is selected from methyl tert-butyl ether, ethyl acetate, hexane, chloroform, dichloromethane, and toluene.

11. The method according to claim 10, wherein in step (c), the liquid chromatography uses a mobile phase selected from an aqueous solution of formic acid, an aqueous solution of acetic acid, and a mixed aqueous solution of acetic acid and ammonium acetate.

12. The method according to claim 10, wherein in step (c), the liquid chromatography uses a C18 column as a stationary phase.

13. The method according to claim 10, wherein in step (c), the liquid chromatography is performed for 3 to 10 minutes.

14. The method according to claim 1, wherein in step (d), the multiple reaction monitoring (MRM) is performed to simultaneously analyze two or more neurotransmitters and/or their metabolites selected from tyrosine (Tyr), 3,4-dihydroxy-I-phenylalanine (L-DOPA), dopamine (DA), 3,4-dihydroxyphenylacetic acid (DOPAC), 3-methoxytyramine (3-MT), homovanillic acid (HVA), epinephrine (EP), 3,4-dihydroxyphenyl glycol (DHPG), metanephrine (MN), 3-methoxy-4-hydroxymandelic acid (VMA), tyramine (TA), octopamine (OA), kynurenine (Kyn), 5-hydroxytryptophan (5-HTP), serotonin (5-HT), 5-hydroxyindole-3-acetic acid (5-HIAA), glutamine (Gln), glutamate (Glu), and γ-aminobutyric acid (GABA).

15. The method according to claim 1, wherein the multiple reaction monitoring (MRM) is performed by detecting hydrogen ions ($H^+$) or ammonium ions ($NH_4^+$) of the neurotransmitters and/or their metabolites.

* * * * *